United States Patent
Yoo et al.

(10) Patent No.: US 11,360,051 B2
(45) Date of Patent: Jun. 14, 2022

(54) CONSTRUCTION STRUCTURE CORROSION MEASUREMENT SENSOR ASSEMBLY AND METHOD FOR MEASURING CORROSION BY USING SAME

(71) Applicant: INDUSTRY-UNIVERSITY COOPERATION FOUNDATION HANYANG UNIVERSITY ERICA CAMPUS, Ansan-si (KR)

(72) Inventors: Bong Young Yoo, Seongnam-si (KR); Soo Bin Park, Ansan-si (KR); Han Seung Lee, Ansan-si (KR); Song Jun Lee, Seoul (KR); Dong Ik Lee, Anyang-si (KR)

(73) Assignee: INDUSTRY-UNIVERSITY COOPERATION FOUNDATION HANYANG UNIVERSITY ERICA CAMPUS, Ansan (KR)

( * ) Notice: Subject to any disclaimer, the term of this patent is extended or adjusted under 35 U.S.C. 154(b) by 568 days.

(21) Appl. No.: 16/314,071

(22) PCT Filed: Nov. 26, 2018

(86) PCT No.: PCT/KR2018/014592
§ 371 (c)(1),
(2) Date: Dec. 28, 2018

(87) PCT Pub. No.: WO2019/182225
PCT Pub. Date: Sep. 26, 2019

(65) Prior Publication Data
US 2021/0231611 A1 Jul. 29, 2021

(30) Foreign Application Priority Data

Mar. 20, 2018 (KR) .................. 10-2018-0031898
Mar. 20, 2018 (KR) .................. 10-2018-0031904
Sep. 12, 2018 (KR) .................. 10-2018-0108743

(51) Int. Cl.
*G01N 27/904* (2021.01)
*G01N 27/90* (2021.01)
*G01N 33/20* (2019.01)

(52) U.S. Cl.
CPC ....... *G01N 27/904* (2013.01); *G01N 27/9006* (2013.01); *G01N 33/20* (2013.01)

(58) Field of Classification Search
CPC ... G01N 27/904; G01N 27/9006; G01N 33/20
USPC ........................................................ 324/240
See application file for complete search history.

(56) References Cited

U.S. PATENT DOCUMENTS 4,942,354 A * 7/1990 Miller .................. G01N 17/02
324/71.2
6,962,082 B2 11/2005 Hashimoto et al.
(Continued)

FOREIGN PATENT DOCUMENTS

CN 107132179 A * 9/2017 ........... G01N 17/006
CN 107132179 A 9/2017
(Continued)

OTHER PUBLICATIONS

Sodano; "Development of an Automated Eddy Current Structural Health Monitoring Technique with an Extended Sensing Region for Corrosion Detection"; Jun. 1, 2007; Structural Health Monitoring; vol. 6, Issue, 2; pp. 111-117 (Year: 2007).*
(Continued)

*Primary Examiner* — Judy Nguyen
*Assistant Examiner* — Rahul Maini
(74) *Attorney, Agent, or Firm* — Sughrue Mion, PLLC

(57) ABSTRACT

The present disclosure provides a construction structure corrosion measurement sensor having accuracy higher than that of conventional sensors, and a method for measuring
(Continued)

corrosion by using the same. To this end, the present disclosure provides a sensor assembly including an eddy-current sensor including an insulator a coil surrounding the outer periphery of the insulator. The present disclosure also provides a construction structure corrosion measurement method including the steps of: positioning a sensor assembly next to a rebar inside a construction structure in parallel with and adjacent to the rebar; applying a voltage to the sensor assembly; measuring a voltage generated by an eddy current resulting from the adjacent rebar; and conducting measurement at a predetermined time interval so as to measure a voltage change.

7 Claims, 9 Drawing Sheets

(56) References Cited

U.S. PATENT DOCUMENTS

| | | | |
|---|---|---|---|
| 8,547,110 B2* | 10/2013 | Kesil | G01N 27/023 |
| | | | 324/633 |
| 2012/0088438 A1* | 4/2012 | Tada | B24B 37/013 |
| | | | 324/234 |

FOREIGN PATENT DOCUMENTS

| | | |
|---|---|---|
| JP | 3205291 B2 | 9/2001 |
| JP | 2004-333330 A | 11/2004 |
| JP | 2006-337231 A | 12/2006 |
| JP | 2009-020058 A | 1/2009 |
| JP | 2010-48723 A | 3/2010 |
| JP | 4423642 B2 | 3/2010 |
| JP | 2011-158438 A | 8/2011 |
| KR | 10-0539380 B1 | 12/2005 |
| KR | 10-0564879 B1 | 3/2006 |

OTHER PUBLICATIONS

Kumar et al.; "Sensor Systems for Corrosion Monitoring in Concrete Structures"; Pub. Date May 29, 2006; Sensors & Transducers Magazine; vol. 67, Issue 5; p. 553-560 (Year: 2006).*

Zhao et al.; Translation of CN-107132179-A; Sep. 2017; Published by EPO and Google (Year: 2017).*

Office Action issued in Korean Patent Application No. 10-2018-0108743 dated Oct. 17, 2019 (not included).

* cited by examiner

CONSTRUCTION STRUCTURE CORROSION MEASUREMENT SENSOR ASSEMBLY AND METHOD FOR MEASURING CORROSION BY USING SAME

TECHNICAL FIELD

The present disclosure relates to a sensor assembly for measuring corrosion of a construction structure and a method for measuring corrosion by using the same and, more particularly, to a sensor assembly having a simple configuration but being capable of measuring corrosion with an accuracy and a reliability higher than those of conventional sensor assemblies, and a method for measuring corrosion by using the same.

BACKGROUND ART

Technology to prolong the life of a construction structure by recognizing the degree of internal corrosion thereof is regarded as important and has been researched accordingly. However, there is a serious difficulty in determining the life of a construction structure in real time. Since it is difficult to recognize the degree of corrosion of a rebar inside a construction without destroying the same, a monitoring scheme based on a nondestructive inspection, for example, is requested.

To this end, a contact-type electrode based on copper sulfate is used on actual construction sites such that a voltage is measured therefrom and compared with that measured from a rebar inside concrete, thereby recognizing the degree of corrosion of the rebar. According to this scheme, corrosion of the rebar forms iron oxide, which changes the electric conductivity and results in a voltage difference from that of the reference electrode. This phenomenon is used to indirectly recognize from the outside whether or not the rebar is corroded.

However, in the case of a contact-type electrode, direct measurement is impossible because measurement is made on the surface of concrete outside the construction, and the fact that measurement is possible only after making a contact results in a time delay and makes instant monitoring difficult. In addition, measurement may be affected by a situation such as the external temperature, meaning that various factors may act as parameters.

DETAILED DESCRIPTION OF THE INVENTION

Technical Problem

An aspect of the present disclosure is to provide a construction structure corrosion measurement sensor having accuracy higher than that of conventional sensors, and a method for measuring corrosion by using the same.

Another aspect of the present disclosure is to provide a construction structure corrosion measurement sensor which uses a less space and thus can increase the degree of utilization of the space inside concrete and improve the stability of the construction structure, and a method for measuring corrosion by using the same.

Another aspect of the present disclosure is to provide a construction structure corrosion measurement sensor configured such that, when a sensor operates erroneously or malfunctions, the error can be identified or corrected by another sensor, thereby improving reliability, and a method for measuring corrosion by using the same.

Technical Solution

In accordance with an aspect of the present disclosure, there is provided a construction structure corrosion measurement sensor assembly including an eddy-current sensor including:

an insulator; and a coil surrounding an outer periphery of the insulator.

The coil is preferably wound to have its turns to be close to each other in the longitudinal direction of the insulator.

The insulator is preferably a hollow insulator.

The hollow insulator preferably has an open circuit potential (OCP) sensor embedded therein.

The open circuit potential sensor is formed as a reference electrode arranged at the center portion of the hollow insulator, which constitutes the eddy-current sensor, along the longitudinal direction of the insulator.

Multiple sensor assemblies may be arranged at a predetermined interval in the longitudinal direction of the rebar.

The coil may be wound around the insulator in two or more layers, thereby increasing the amount of generated eddy current and improving the measurement sensitivity.

In accordance with another aspect of the present disclosure, there is provided a construction structure corrosion measurement method including the steps of:

positioning a sensor assembly next to a rebar inside a construction structure in parallel with and adjacent to the rebar;

applying a voltage to the sensor assembly;

measuring a voltage generated by an eddy current resulting from the adjacent rebar; and conducting measurement at a predetermined time interval so as to measure a voltage change.

The sensor assembly may be an eddy-current sensor.

The sensor assembly preferably further includes an open circuit potential sensor.

According to the present disclosure, a sensor is positioned horizontally next to a rebar inside concrete, unlike the conventional manner of measuring corrosion from the outside in a direction perpendicular to the rebar. An AC voltage having a specific frequency is applied to both ends of the sensor, and the corrosion state is measured by measuring the voltage change resulting from the eddy current that varies depending on the composition of the rebar, which changes as corrosion proceeds.

It is more preferable to measure both a changing voltage through an eddy-current sensor and to measure a changing voltage through an open circuit potential sensor, and the degree of corrosion of the rebar can be rendered into a numerical value in this manner.

Meanwhile, the type of the coil used for the sensor assembly, such as the length of the coil and the number of windings, varies depending on the type of the construction structure, the environment in which the same is positioned, and the characteristics of the rebar used for the structure. The specification of the sensor is varied accordingly.

The magnetic field generated by the coil has a limited range, and the present disclosure utilizes the eddy current on a side surface of the coil. Therefore, the smaller the distance between the rebar and the coil is, the more advantageous it becomes.

The sensor adapted to the environment is used to measure the voltage and the eddy current that changes when the component of the rebar varies as corrosion of the rebar proceeds.

In addition, according to the present disclosure, an eddy-current sensor and an open circuit potential sensor may be combined to improve the accuracy of corrosion measurement. That is, even if one sensor operates erroneously, a measurement value can be secured by the other sensor, thereby maintaining stable measurement.

Furthermore, a voltage measured by the eddy-current sensor and a voltage measured by the open circuit potential sensor may be combined, thereby improving the reliability of the measurement value. For example, the voltage measured by the eddy-current sensor and the voltage measured by the open circuit potential sensor may be averaged, thereby obtaining the final measurement value. Alternatively, the voltage measured by the eddy-current sensor and the voltage measured by the open circuit potential sensor may be averaged after endowing one of the voltages with a weight.

Meanwhile, according to the present disclosure, equipment using a wireless network, such as a portable device, may be integrated with the sensor assembly and used for measurement, making it possible to expect expandability in usage.

Advantageous Effects

According to the present disclosure, a sensor is positioned inside a construction structure such that corrosion is measured at a distance smaller than in the conventional manner of measuring the same from outside through an electrode, thereby improving the measurement accuracy.

In addition, a coil is positioned in parallel with the rebar such that the size of the occupied space is substantially smaller than when the same is positioned vertically, thereby improving the degree of utilization of the space inside the concrete and the stability of the construction structure.

Furthermore, measurement through an eddy current and measurement through an open circuit proceed simultaneously, thereby improving measurement accuracy, and, even if one sensor operates erroneously or malfunctions, operation is guaranteed, thereby improving measurement reliability.

MODE FOR CARRYING OUT THE INVENTION

Hereinafter, a preferred embodiment of the present disclosure will be described in detail with reference to the accompanying drawings.

Figure 1:
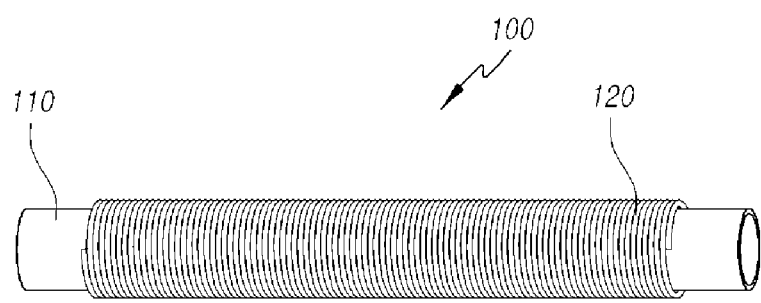
FIG. 1 illustrates a sensor assembly according to a preferred embodiment of the present disclosure.

FIG. 1 illustrates a sensor assembly according to an embodiment of the present disclosure.

The sensor assembly 100 is an eddy-current sensor including an insulator 110 and coil 120.

The coil 120 is wound outside the insulator 110. The coil 120 is wound to have its turns to be close to each other in the longitudinal direction of the insulator. Both ends of the coil 120 are connected to a function generator for applying a voltage and a digital multimeter (DMM) for detecting an eddy current.

The insulator 110 has the shape of a hollow cylinder and is made of acrylic resin. However, the material or shape is not limited as long as the same can function as an insulator. The insulator may also have a quadrangular section.

Figure 2:
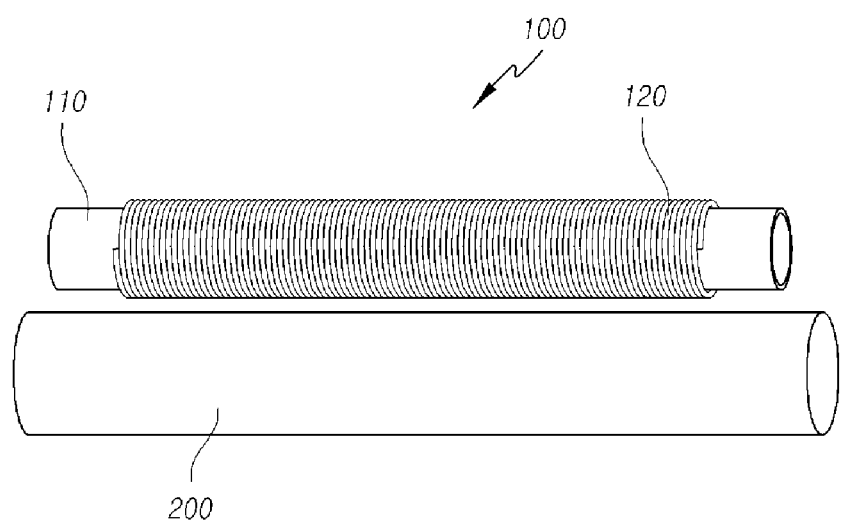
FIG. 2 illustrates a state in which the sensor assembly of FIG. 1 is arranged adjacent to a rebar.

FIG. 2 illustrates a state in which the sensor assembly of FIG. 1 is arranged next to a rebar inside a construction structure.

The sensor assembly 100 is arranged at a predetermined interval from and in parallel with (in the other words, side by side) a rebar 200 inside concrete.

Each sensor assembly 100 has a coil 120 installed to be drawn out of the concrete.

An appropriate number of sensor assemblies 100 may be arranged in the longitudinal direction of the rebar 200.

Figure 3:
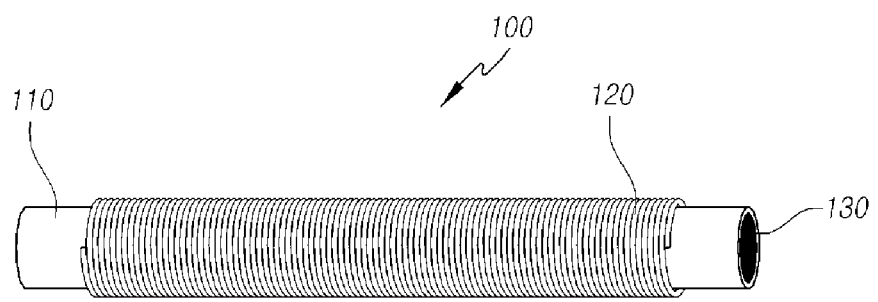
FIG. 3 illustrates a sensor assembly according to another embodiment of the present disclosure.

Meanwhile, as illustrated in FIG. 3, the sensor assembly 100 preferably includes an open circuit potential sensor 130 in addition to the eddy-current sensor including an insulator 110 and a coil 120.

The open circuit potential sensor 130 is formed as an electrode inserted into the insulator 110.

Figure 4:
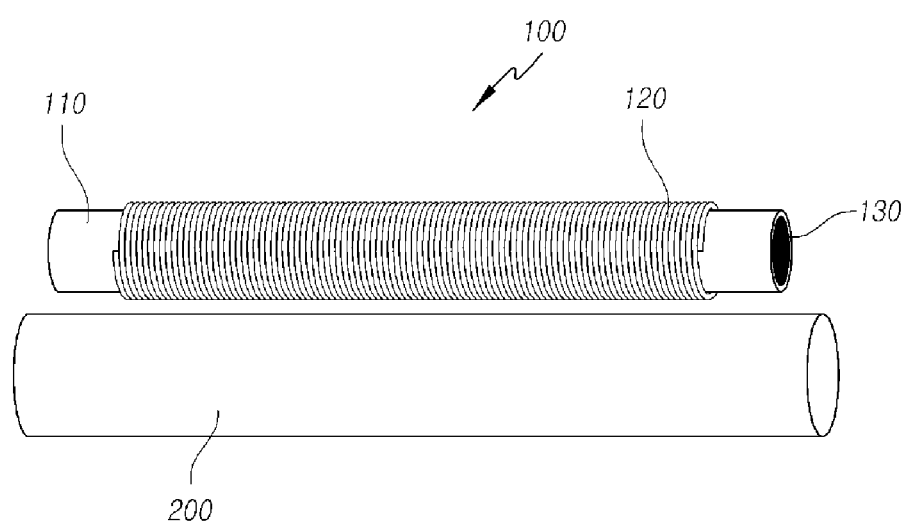
FIG. 4 illustrates a state in which the sensor assembly of FIG. 3 is arranged adjacent to a rebar.

FIG. 4 illustrates a conceptual state in which the sensor assembly of FIG. 3 is arranged inside a construction structure. In this case, the sensor assembly 100 is arranged in the same manner as when the same solely includes an eddy-current sensor. In other words, the same is arranged at a predetermined interval from and in parallel with a rebar 200.

A method for measuring corrosion of a construction structure by using a sensor assembly 100 will now be described.

Firstly, a simulation was performed to confirm whether or not it is possible to use an eddy current in order to check the corrosion state of a construction according to the present disclosure.

To this end, an eddy-current simulation was performed by using a coil and a rebar. The coil was positioned near the rebar, and an AC voltage of 4.9 MHz and 5 Vrms was applied to the coil.

As a result, it was confirmed that application of the AC voltage to the coil generated a current in the rebar. The coil and the rebar were spaced apart from each other, and the rebar had no circuit formed therein, meaning that no current could flow through the rebar. Accordingly, it was confirmed that the generated current was an eddy current resulting from the AC voltage applied to the coil. This confirmed that the corrosion state of the rebar surface could be detected by using an eddy current.

On the basis of such a result, an experiment for specifically measuring the corrosion state of a rebar was performed.

Firstly, an eddy-current sensor including an acrylic resin hollow insulator and a coil wound around the same was prepared as a sensor assembly as illustrated in FIG. 1.

Two experiments were performed, including an experiment inside a water container simulating a concrete environment and an experiment regarding actual concrete.

Figure 5:
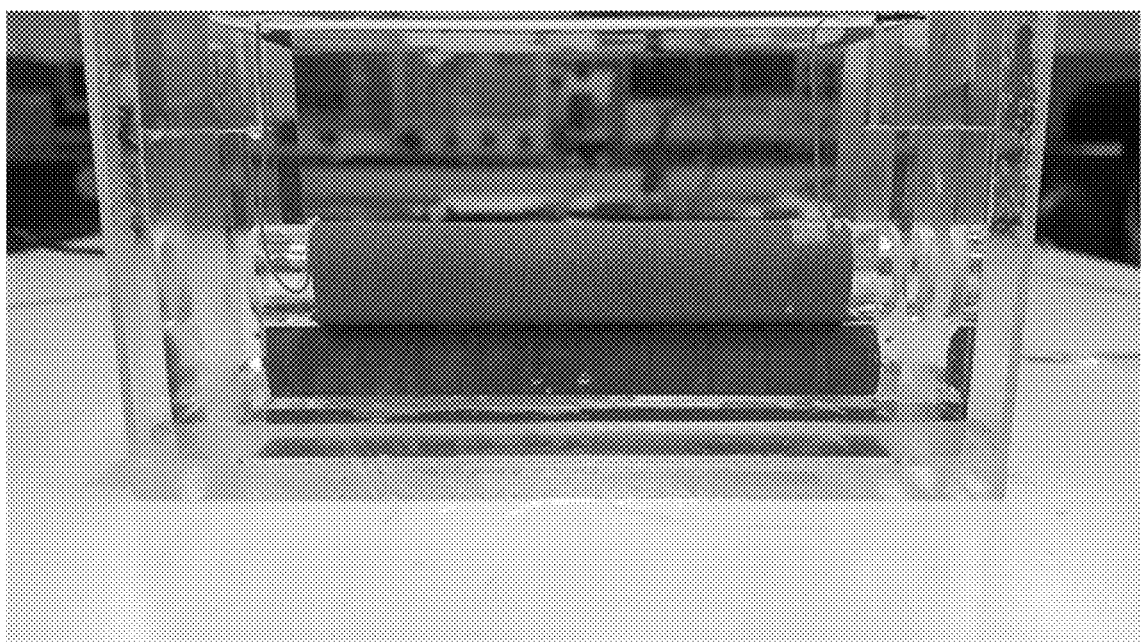
FIG. 5 is a photograph of a device for conducting a corrosion experiment according to an embodiment of the present disclosure.

The experiment inside a water container was conducted, as illustrated in FIG. 5, by immersing a rebar in a water container and by measuring the voltage change over a predetermined period of time such that an actual situation is simulated.

The rebar used for experiment had the specification including a weight of 86.55 g, a diameter of 13 mm, and a length of 10 cm.

As the coil constituting the eddy-current sensor for the experiment, a copper coil having a thickness of 0.32 mm and a length of 8 cm was wound around the outer peripheral surface of a circular hollow insulator (having a diameter of 15 mm). Both ends of the coil were connected to a function generator and to a digital multimeter, respectively.

The water container had the specification including a height of 4 cm, and was filled with NaCl 3.5% solution. The solution was replaced once during the experiment period in order to maintain the concentration.

Under such conditions, a signal of 1 MHz and 10V was generated by the function generator, and an AC voltage was applied to the coil. The voltage caused by the resulting eddy current was measured by the digital multimeter connected to the coil, thereby checking the corrosion condition of the rebar. The experiment was conducted over 66 days.

As a result, buildup of scale on the rebar and on the coil was confirmed on the $29^{th}$ day, and it was confirmed on the $66^{th}$ day that the scale increased and began to accumulate on the bottom. It was also confirmed that the lump of scale adhering to a part of the acrylic hollow body, which is a hollow insulator, near the rebar was increasing, and the area of scale adhering to the coil was also expanding.

Figure 6:
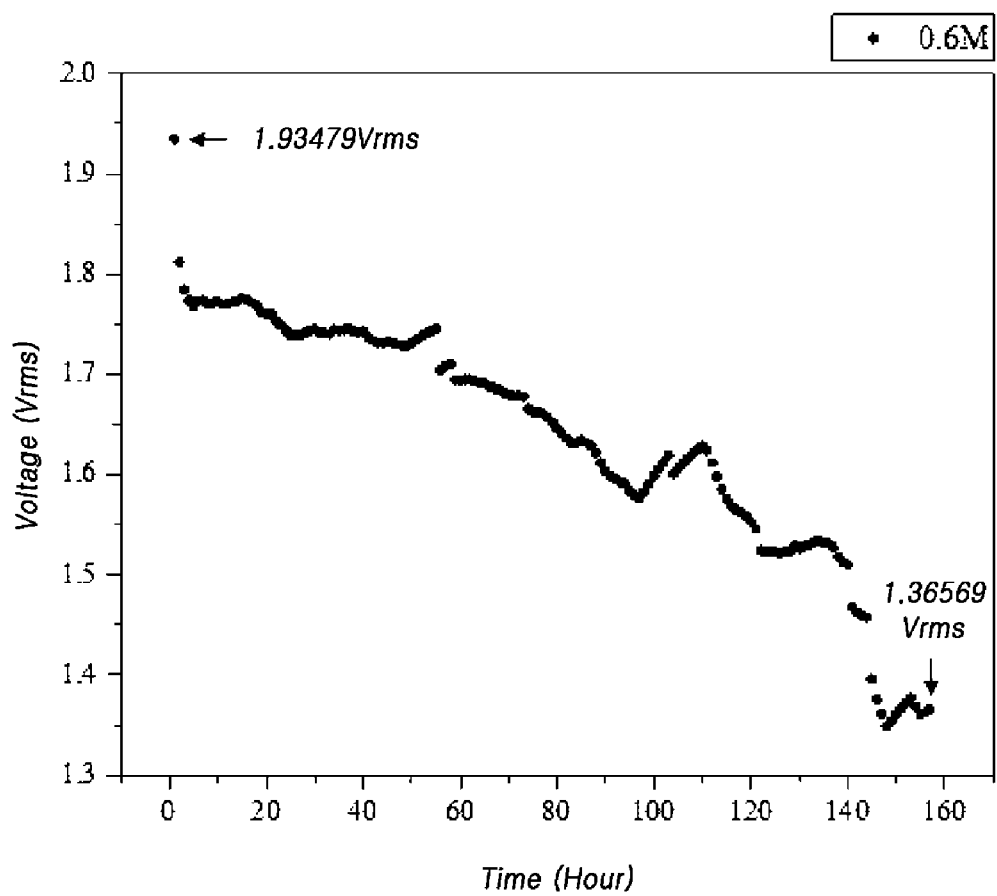
FIG. 6 is a graph illustrating the result of measuring a change in voltage of an eddy current over time in connection with the embodiment of FIG. 5.

FIG. 6 is a graph illustrating the result of evaluating eddy-current measurement characteristics as the rebar is corroded in such a manner.

It is obvious from the graph that, as time elapses, the voltage resulting from the measured eddy current decreases continuously. It was confirmed that the voltage of 1.93479 Vrms detected during the initial measurement decreased to 1.36569 Vrms after 160 hours. As such, the corrosion situation of the rebar can be checked by sensing the voltage resulting from the eddy current generated by the interaction between the coil and the rebar.

Meanwhile, since the sensor assembly according to the present disclosure is arranged at a predetermined interval from and in parallel with a rebar, the measurement sensitivity may vary depending on the distance between the sensor assembly and the rebar. If the distance between the rebar and the sensor assembly is too large, no eddy current is generated; if the distance is too small, the coil may be affected by corrosion on the surface of the rebar. In view of such a relationship, the preferred interval between the sensor assembly and the rebar is up to about 0.12 cm.

In addition, the voltage applied to the sensor assembly and the voltage generated by the eddy current resulting therefrom are affected by the frequency generated by the function generator. In order to confirm such an influence, voltage changes were measured in connection with various frequencies.

Firstly, a function generator and a digital multimeter were connected to both ends of a coil constituting an eddy-current sensor. The applied voltage was fixed at 5 Vrms, and the voltage was measured in the absence of a rebar while changing the frequency from 100 kHz to 6 MHz by 100 kHz. In addition, a rebar was positioned on a side surface of the coil, and the voltage was then measured by changing the frequency from 100 kHz to 6 MHz by 100 kHz in the same manner.

Figure 7:
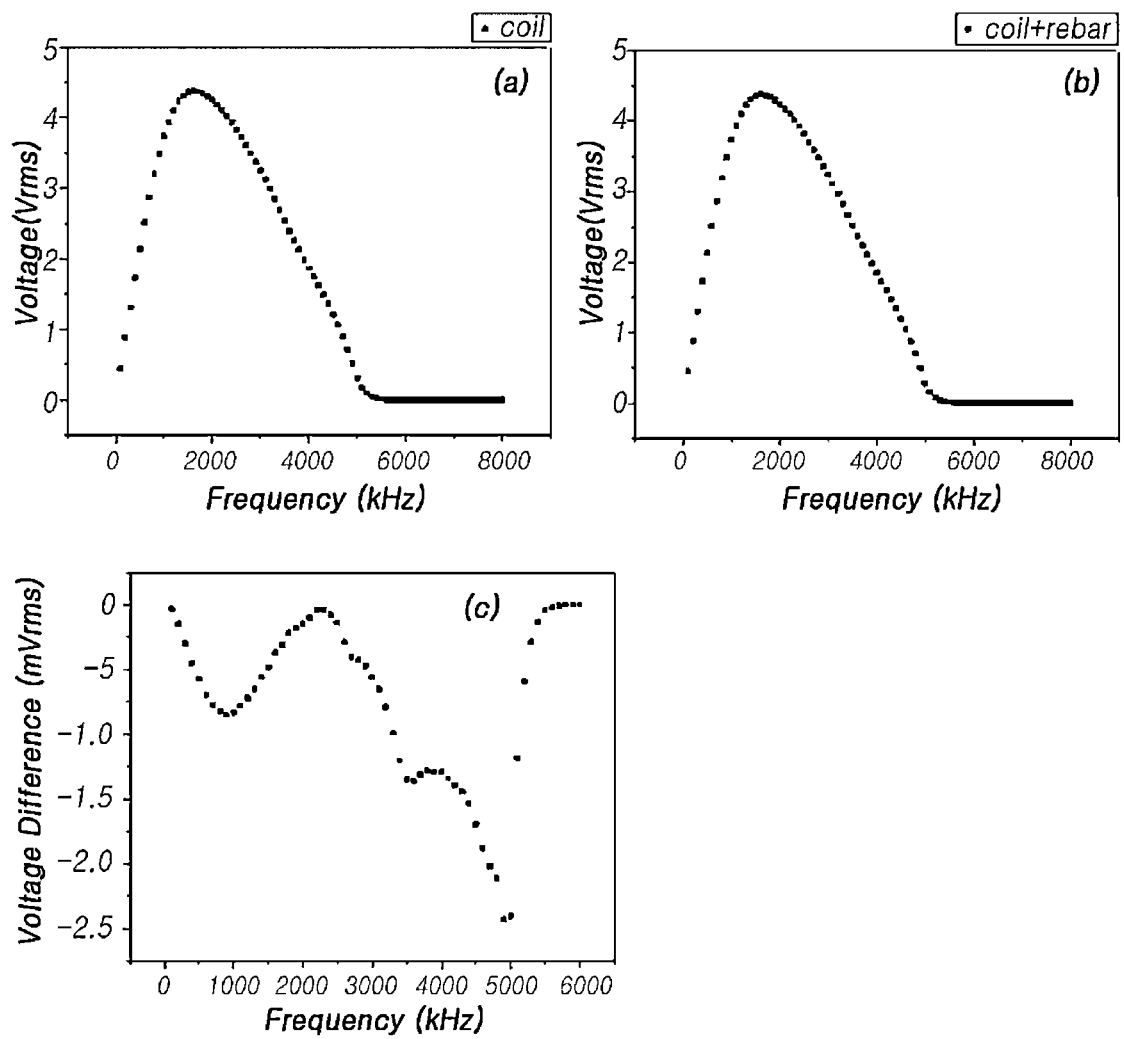
FIG. 7 is a graph illustrating a change in voltage of an eddy current in connection with a frequency generated by a function generator according to an embodiment of the present disclosure.

In FIG. 7, (a) refers to a graph illustrating the voltage measured in connection with the frequency in the case of a sensor assembly having no rebar in the periphery; (b) refers to a graph illustrating the voltage measured in connection with the frequency when a rebar is positioned adjacent to the sensor assembly; and (c) refers to a graph illustrating the difference in voltage, with regard to each frequency, between the case of (a) in which no rebar exits and the case of (b) in which a rebar exists.

It was confirmed as a result of measuring the difference in voltage between the case in which a rebar exists and the case in which no rebar exists that an eddy current was generated as the rebar approached the coil, and the effective voltage measured from the coil was affected by the eddy current. The larger an amount of eddy current generated, the larger a change in the effective voltage occurs, thereby making it possible to measure the corrosion of the rebar more sensitively. It is obvious from (c) of FIG. 7 that the difference in voltage between the case in which a rebar exists and the case in which no rebar exists is largest when the frequency is in the range of 3.3-4.9 MHz. This means that the largest eddy current was generated. In other words, the measurement sensitivity is most excellent in this frequency range. It was confirmed that 4.9 MHz, in particular, was the optimal frequency.

Figure 8:
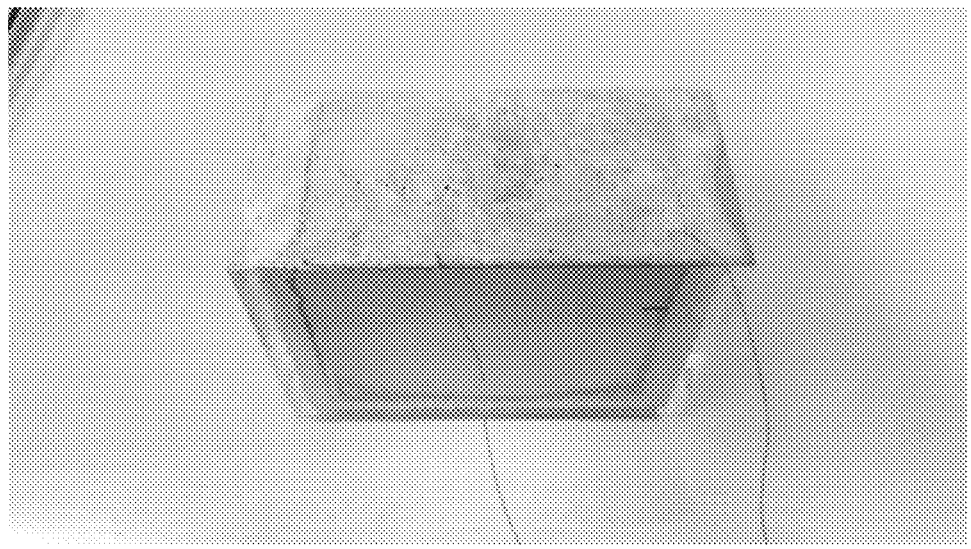
FIG. 8 is a photograph of concrete including an actual rebar and a sensor assembly according to an embodiment of the present disclosure.

Next, as an experiment adapted to an actual environment, a sensor assembly and a rebar were placed side by side in a water container having a height of 8 cm, and concrete was poured therein. The used rebar had the specification including a diameter of 13 mm and a length of 10 cm. As a result, concrete having the sensor assembly and the rebar embedded therein was obtained as in FIG. 8.

In addition, in order to accelerate corrosion of the rebar, 3 ml of NaCl 3.5% solution was supplied from the concrete surface once a day. The experiment was conducted over eight days, and the result is illustrated in FIG. 9.

Figure 9:
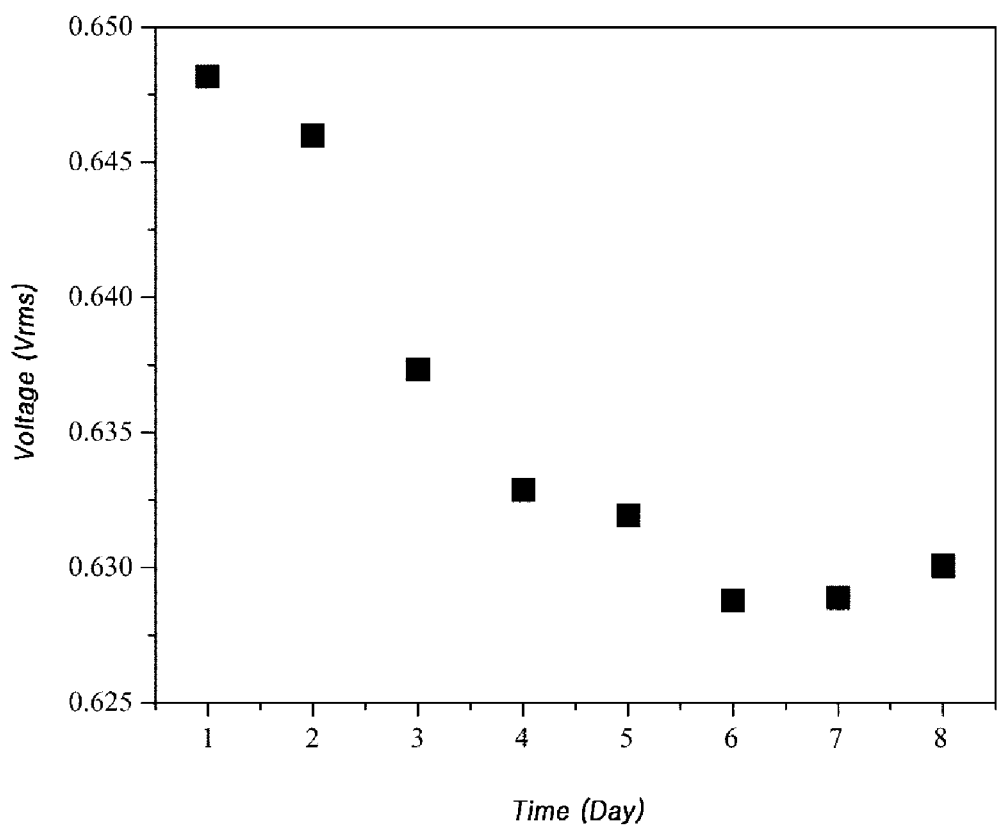
FIG. 9 is a graph illustrating the result of measuring a change in voltage of an eddy current over time when a sensor assembly and a rebar remain inserted into actual concrete in connection with the embodiment of FIG. 8.

It is obvious from the graph of FIG. 9 that the effective voltage measured by the digital multimeter during the experiment period was reduced by about 20 mV.

This is the result of infiltration of NaCl solution into the concrete and following corrosion of the rebar. As such, the result of experiment involving concrete pouring confirms that, as in the case of the simulation inside a water container, the sensor assembly according to the present disclosure is appropriate for detecting rebar corrosion.

Meanwhile, another embodiment of the present disclosure includes an open circuit potential sensor inside a hollow insulator of a sensor assembly. The open circuit potential sensor is configured as a rod-shaped electrode, which is used to detect an output voltage with regard to an applied voltage.

The measurement value from the eddy-current sensor and the measurement value from the open circuit potential sensor may be used together.

The arithmetic mean value of the measurement values from the two sensors may be used to check the corrosion situation. Alternatively, in view of the fact that the output voltages from respective sensors have different changes or sensitivities, the two may be averaged after endowing one of the two with a weight.

Such a combination of two sensors can improve the accuracy of measurement. In addition, even if one sensor malfunctions, the measurement system can be maintained stably by operating the other sensor.

CROSS-REFERENCE TO RELATED APPLICATION

If applicable, this patent application claims priorities under 35 U.S.C § 119(a) of Patent Application No. 10-2018-0031904 filed on Mar. 20, 2018 in Korea, Patent Application No. 10-2018-0031898 filed on Mar. 20, 2018 in Korea, and Patent Application No. 10-2018-0108743 filed on Sep. 12, 2018 in Korea, the entire contents of which are incorporated herein by reference. In addition, this non-provisional application claims priorities in countries, other than the U.S., with the same reason based on the Korean Patent Applications, the entire contents of which are hereby incorporated by reference.

The invention claimed is:

1. A construction structure corrosion measurement method comprising:
    positioning a sensor assembly next to a rebar inside a construction structure in parallel with and adjacent to the rebar;
    applying a voltage to the sensor assembly;
    measuring a voltage generated by an eddy current sensor resulting from an eddy current in the rebar adjacent to the sensor assembly;
    measuring a voltage by an open circuit potential (OCP) sensor of the sensor assembly; and
    conducting measurements at a predetermined time interval so as to measure a voltage change, wherein a first average between a first voltage measured by the eddy current sensor and a first voltage measured by the OCP sensor at a first time is compared to a second average between a second voltage measured by the eddy current sensor and a second voltage measured by the OCP sensor at a second time; and
    determining a degree of corrosion based on the voltage change.

2. The construction structure corrosion measurement method as claimed in claim 1, wherein the sensor assembly configured to measure the eddy current comprises an insulator and a coil surrounding an outer periphery of the insulator.

3. The construction structure corrosion measurement method as claimed in claim 2, wherein the OCP sensor is provided inside the insulator.

4. The construction structure corrosion measurement method as claimed in claim 1, wherein the first and second averages are obtained after endowing one of the voltages measured by either the eddy current sensor or the OCP sensor with a weight.

5. The construction structure corrosion measurement method as claimed in claim 1, wherein the voltage change is obtained by generating an AC voltage at a specific frequency by a function generator and by measuring a voltage of an eddy current generated by the sensor assembly.

6. The construction structure corrosion measurement method as claimed in claim 5, wherein the AC voltage generated by the function generator has a frequency of 3.3-4.9 MHz.

7. The construction structure corrosion measurement method as claimed in claim 1, wherein the rebar and the sensor assembly are spaced apart from each other by a distance of 0.12 cm or less.

* * * * *